United States Patent [19]

Stroebel et al.

[11] Patent Number: 4,588,396
[45] Date of Patent: May 13, 1986

[54] APPARATUS FOR GRAVITY FEED OF LIQUID UNDER CONSTANT HYDROSTATIC PRESSURE

[76] Inventors: Maurice G. Stroebel; Terryl T. Stroebel, both of Rte. 1, Danvers, Minn. 56231

[21] Appl. No.: 528,048

[22] Filed: Aug. 31, 1983

Related U.S. Application Data

[63] Continuation-in-part of Ser. No. 436,007, Oct. 22, 1982, abandoned.

[51] Int. Cl.⁴ ............................................. A61M 5/00
[52] U.S. Cl. ................................. 604/246; 604/244; 604/257; 604/414
[58] Field of Search ............... 604/246, 257, 251, 51, 604/244, 403, 411–415; 137/453, 454

[56] References Cited

U.S. PATENT DOCUMENTS

| | | | |
|---|---|---|---|
| 2,850,211 | 9/1958 | Fernandez | 604/251 X |
| 3,216,419 | 11/1965 | Scislowicz | 604/257 |
| 3,929,157 | 12/1975 | Serur | 604/246 X |
| 4,078,563 | 3/1978 | Tuseth | 604/246 X |
| 4,198,971 | 4/1980 | Noiles | 604/251 X |
| 4,325,368 | 4/1982 | Kaemmerer | 604/251 X |
| 4,425,123 | 1/1984 | Di Salvo | 604/251 X |

OTHER PUBLICATIONS

The Journal of the American Oil Chemists' Society, Jul. 1961, issue, Vol. XXXVIII, No. 7, p. 380.

Primary Examiner—Stephen C. Pellegrino
Attorney, Agent, or Firm—James R. Cwayna

[57] ABSTRACT

An inverted liquid supply bottle containing liquid to be dispensed has a downwardly opening neck portion. In one form of the invention, a supply bottle support cup forms a reservoir defining a basin, an upper portion of which is nominally open to the atmosphere. The cup supports the bottle to position the bottom of the downwardly extending neck portion in spaced relation to the bottom of the cup. A liquid feed tube in the form of a capillary tube opens downwardly from the bottom of the reservoir basin and feeds into a transparent sight glass. A flexible deformable liquid delivery tube or hose carries the liquid being dispensed from the bottom of the sight glass to a location for use, and a manually operable hose clamp valve on the hose regulates the rate of flow of the liquid through the hose. In a second form, a reservoir providing a basin is situated below and spaced from the bottle neck. A liquid supply tube extends from inside of the bottle in sealing relationship to the neck portion and into the reservoir to terminate in the basin spaced from the bottom of the basin. A liquid delivery tube extends from the bottom of the basin into a conduit which delivers the liquid being dispensed to a location for use. In either form of the invention, the hose clamp on the outlet hose can be eliminated and flow can be controlled by controlling access of atmospheric pressure to the upper portion of the reservoir basin.

8 Claims, 6 Drawing Figures

APPARATUS FOR GRAVITY FEED OF LIQUID UNDER CONSTANT HYDROSTATIC PRESSURE

This application is a continuation-in-part of our copending application Ser. No. 06/436,007 filed Oct. 22, 1982 now abandoned.

BACKGROUND OF THE INVENTION

1. Field of the Invention.

This invention has relation to the dispensing of liquids by gravity at measured or fixed rates. The invention presents an apparatus which, when properly and accurately initially adjusted, will continue to feed liquid indefinitely at the same rate regardless of the source or height of liquid in the main supply chamber from which the liquid is being supplied.

2. Description of the Prior Art.

It has long been known to feed a liquid to be dispensed from a bottom of a liquid supply container which is suspended or supported above the point to which the dispensed liquid is to be delivered. Where the volume of liquid to be dispensed is relatively small per unit of time, the liquid flows from the supply container through a flexible deformable liquid delivery hose. An adjustable hose clamp valve encompasses the hose at a convenient location, and is manually adjustable to control the rate of discharge of the dispensed liquid from the supply container. Typically such supply containers are open to the atmosphere. As the level of liquid in the supply container drops due to the liquid flowing out of the container, the hydrostatic pressure decreases, and the adjustable hose clamp valve must be continuously adjusted to compensate for this pressure drop in order to attempt to maintain a uniform output from the supply container. As a result, in critical applications, such as the delivery of blood plasma to a living patient, an attendant skilled in the adjustment of the adjustable hose clamp valve must be almost constantly in attendance.

In order to feed liquids to be dispensed at uniform and/or variably controllable rates either by gravity or under otherwise induced pressure, expensive, complicated and relatively difficult to maintain measuring, metering and/or pumping devices have been developed. Relatively close precision can be obtained with some devices in this category; but because of expense, the bulk of such devices, and, consequently, the inability to have such devices available at the time and place they are needed has rendered them unsatisfactory for general usage.

Because of the necessity to constantly adjust the liquid supply flow valve with the constantly changing head of hydrostatic pressure to maintain uniform flow, it has been impossible to calibrate such a valve to control the flow from a liquid supply container into another body of liquid to make the feed of liquid from the liquid supply container proportional to the flow in the other body of liquid. For example, until the present invention, it has not been possible to provide a liquid supply flow valve in a gravity feed liquid supply apparatus which can be proportionally moved toward open and toward closed as flow of water in a municipal water supply increases and decreases.

It has been proposed to meter liquids in the laboratory by connecting the bottom of a large burette with a flexible hose connected to a capillary tube and to introduce air through the sealed top of the burette and down a thin capillary tube to a point near the bottom of the burette. In order to use this apparatus without completely disassembling it, an open sump tank, a siphon conduit open to the interior of the burette, and a pump open from the sump tank into the interior of the top of the burette must be provided. See reprint from *The Journal of the American Oil Chemists' Society*, July 1961 issue, Volume XXXVIII, No. 7, Page 380. Because this article appeared in July of 1961, and since it is not widely used today, it evidently did not render obvious the structure of the present invention.

No specific search was made on this invention; but the applicants and those in privity with them are aware of no prior art which is closer than that discussed above, and are aware of no prior art which anticipates the claims herein.

SUMMARY OF THE INVENTION

An apparatus for gravity feed of liquid under constant hydrostatic pressure includes an inverted liquid-tight liquid supply bottle containing a liquid to be dispensed and having a downwardly opening neck portion, a reservoir defining a basin below the bottle neck portion, and a liquid supply passage between the neck of the bottle and a position within the reservoir basin. An upper portion of the reservoir basin is open to the atmosphere. A liquid delivery tube or hose opens downwardly from the bottom of the reservoir basin and conveys the liquid to be dispensed from the bottom of the basin to a location for use. In one form of the invention shown, the flow of liquid in the liquid delivery tube or hose is controlled by manually adjustable valve means in the liquid delivery line. In another form of the invention, the flow of liquid is controlled by controlling the access of atmospheric air to the reservoir.

In either form, the liquid to be dispensed flows from the liquid supply bottle into the reservoir basin until the bottom end of the liquid supply passage is covered sufficiently to prevent the entry of air back into the bottle. As liquid is removed from the bottom of the basin, more liquid flows from the bottle as air enters the bottle, and an equilibrium is established whereby the height of the liquid pool in the basin varies only slightly around the bottom of the liquid supply passage as the apparatus is used.

Because the reservoir basin is open to the atmosphere, the hydrostatic pressure developed at the discharge point of the liquid delivery tube or hose is measured by the vertical distance from the top of the liquid pool in the reservoir basin (which doesn't vary appreciably) to the location for discharge of the liquid from the hose. Therefore, the hydrostatic pressure exerted at this delivery point is completely unrelated to the height of the liquid in the liquid supply bottle at any time. This allows a single setting of a manually operable adjustable hose clamp valve, for example, to be adjusted once to achieve the rate of flow conditions desired. With such an adjustment, with the viscosity of the liquid kept constant, and with the discharge point of the liquid delivery hose remaining in a single horizontal plane, the flow from the apparatus will be uniform regardless of the quantity of liquid dispensed through the apparatus and regardless of the height of the liquid in the liquid supply bottle.

The same variable control overflow from the apparatus can be obtained without the use of a valve in the liquid delivery tube. Instead, the access of atmospheric pressure to the reservoir basin can be through an adjustable gas flow control valve. This limits the rate at which the air can enter the liquid supply bottle and, therefore, the rate of delivery of liquid from the delivery tube.

In many situations, it is desirable to vary the rate of flow of gravity dispensed liquid with variations of the rate of flow of a larger body of liquid into which the dispensed liquid is being introduced. In accordance with the present invention, since the hydrostatic pressure developed within the apparatus at the point of discharge from the apparatus is not any longer a variable, it is now possible to accurately calibrate a variable flow valve in the liquid delivery conduit or in the atmospheric pressure access line. This valve can then be mechanically or otherwise adjusted in accordance with these calibrations so that the rate of flow from the apparatus is a function of the rate of flow of the body of liquid into which the liquid is being dispensed.

DETAILED DESCRIPTION OF THE PREFERRED EMBODIMENTS

Figure 1:
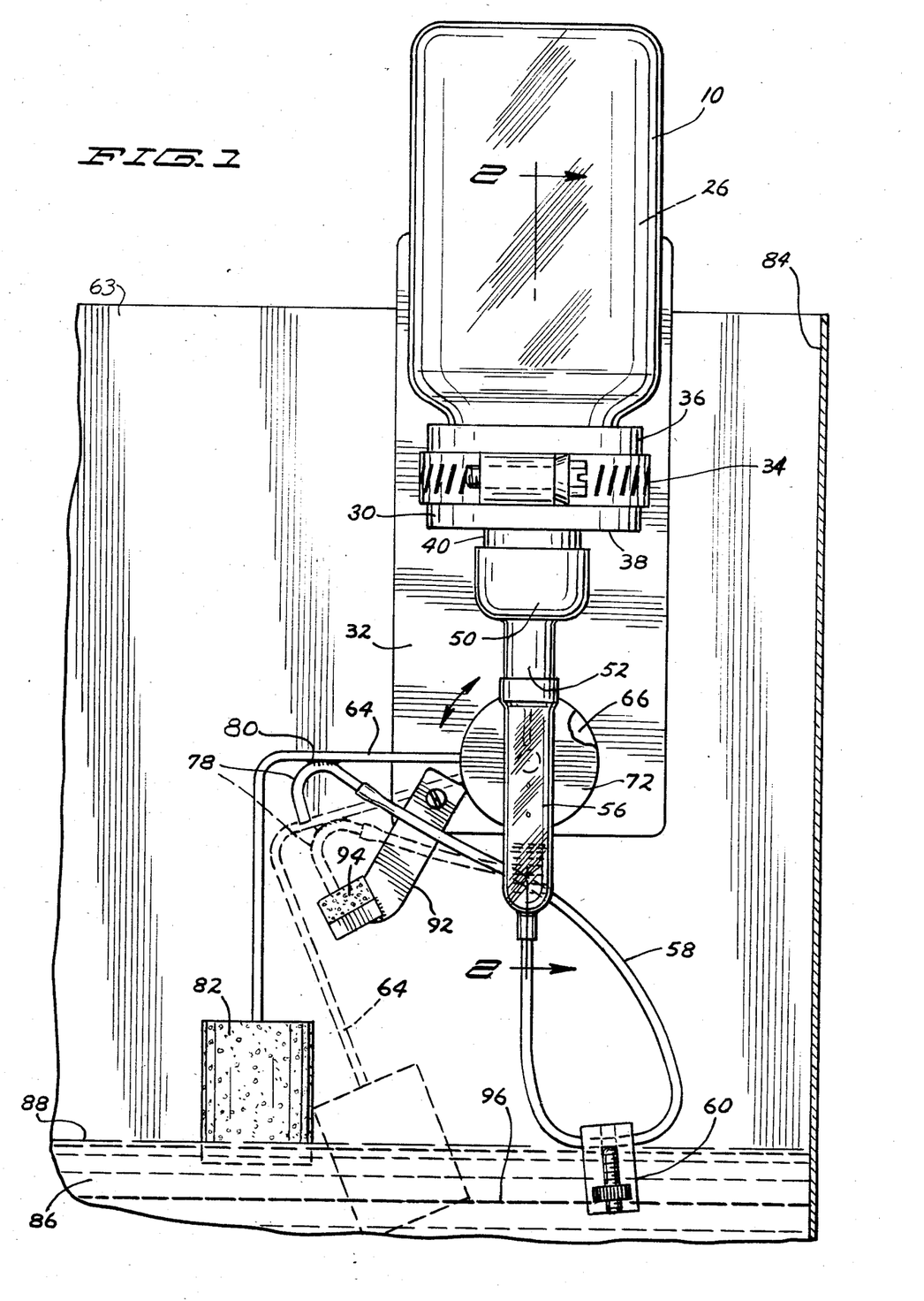
FIG. 1 is an elevational view of an apparatus for gravity feed of liquid under constant hydrostatic pressure according to a first form of the invention useful for introducing liquid medicine or dietary supplements into the drinking water for livestock.
Figure 2:
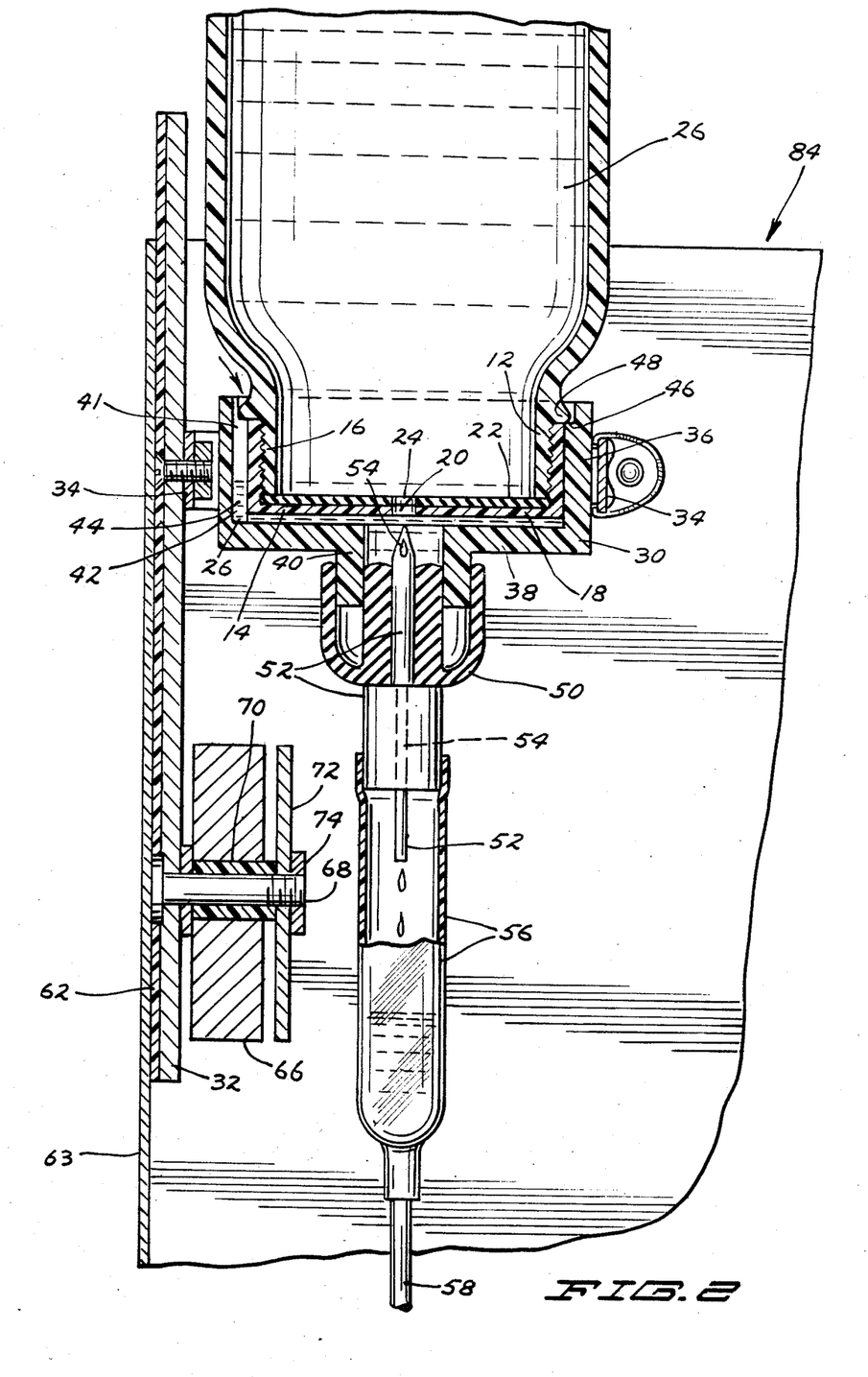
FIG. 2 is an enlarged vertical sectional view taken on the line 2—2 in FIG. 1.

First Form of the Invention:

In the first form of the invention as seen in FIGS. 1 and 2, a liquid supply chamber or bottle 10 is provided with an externally threaded neck portion 12 onto which is screwed a chamber cap or bottle cap 14. This cap has an internally threaded skirt portion 16 and a flat closure portion 18. This closure portion is provided with a central liquid and air supply passage 20 therethrough. A flat gasket 22 is situated between the interior surface of the flat closure portion 18 of the cap 14 and the bottom edge of the neck portion 12 of the supply chamber 10 to insure a tight seal between the two. This gasket 22 is provided with a liquid and air supply passage 24 aligned with the passage 20 in the cap 14.

In order to be ready for use, the supply chamber or bottle 10 is filled with a liquid 26 to be dispensed, and the chamber cap 14 with gasket 22 are screwed tightly in place.

In this form of the invention, a supply chamber support cup 30 is fixedly supported on a vertical base plate 32 through the instrumentality of a cup support clamp 34. The support cup 30 is provided with an upstanding generally cylindrical skirt portion 36, a flat horizontally positioned closure 38, and a neck portion 40 depending downwardly from a central location on the closure portion 38.

The support cup 30 forms a reservoir defining an atmospheric pressure basin 42. The cylindrical skirt portion 36 of the supply chamber support cup 30 is relieved at least at one point to provide an opening 41 in clearing relation to the outside surface of the liquid supply chamber cap skirt portion 16. This opening is within the basin 42 so that the basin is open to the atmosphere.

The skirt portion 36 of the support cup 30 and the skirt portion 16 of the chamber cap 14 are of size and configuration such that when the liquid supply chamber 10 is inverted, internal surfaces of the cup skirt portion 36 will snugly receive the external portions of the cap skirt portion 16, firmly holding the cap and supply chamber in inverted position as seen in FIGS. 1 and 2. A shoulder 46 provided on the cup skirt portion 36 contacts an outwardly extending protuberance 48 on the chamber neck portion 12 to hold the flat closure portion 18 of the chamber cap 14 in spaced relation to the flat closure portion 38 of the supply chamber support cup 30.

A rubber stopper 50 is situated in downwardly extending sealing relation to the support cup neck portion 40 and is provided with a liquid feed and drip tube 52 extending therethrough. The feed tube 52 has a substantially vertical liquid feed opening 54 therethrough.

A transparent cylindrical sight glass 56 is situated in sealing relationship to the feed tube 52 and encompasses the bottom portion of that tube.

A flexible deformable liquid delivery hose 58 is open to and extends downwardly from the bottom of the sight glass 56. An adjustable hose clamp valve 60 is positioned on the hose 58 to regulate the amount of flow of liquid therethrough.

For many uses of the apparatus of the invention, the aforementioned elements will be sufficient to accomplish the purpose of the invention. For example, whenever the feed from the apparatus is to be at an uniform *and continuous* rate, the liquid delivery hose 58 can be positioned to discharge into the area where the liquid 26 is to be fed. The liquid supply chamber 10, after being filled with liquid 26 to be dispensed and with the chamber cap 14 in place, can be inverted and inserted into its support cup 30. Liquid 26 will flow through the liquid-/air supply passages 20 and 24 of the chamber cap 14 and gasket 22, respectively, to form a liquid pool 44 in atmospheric pressure basin 42. When this pool 44 reaches a height such that air cannot pass back through the reservoir and up into the supply chamber 10 through the liquid and air supply passage 20 and where the vaccuum created in the inverted bottom (now top) of the supply chamber 10 prevents further flow of liquid out of the chamber, an equilibrium is established. As liquid 26 leaves the basin through liquid feed tube 52, lowering the level of liquid pool 44, air will enter from opening 41 and pass up through liquid/air supply passage 22. This relieves the vacuum in bottle 10 and allows more liquid to come down to reestablish equilibrium.

The metering of the flow of liquid out through the hose 58 is commonly controlled by measuring the number of drops forming at and falling from the bottom of the liquid feed and drip tube 52 through the sight glass 56 and into the liquid delivery hose 58 in a predetermined time period. This is done by adjusting the hose clamp valve 60 to give the number of drops per minute, for example, representing the desired rate of liquid flow.

As the apparatus operates, only the variation in the height of the liquid in the pool 44 in basin 42 will act to change the hydrostatic delivery pressure which is measured from the top of that liquid pool to the delivery point at the far end of the flexible hose 58. The height of fluid in the basin 42 changes by a few millimeters, and so can be said as a practical matter to remain constant.

The hydrostatic pressure head developed between the top of liquid 26 in pool 44 in the basin 42 and the output end of the liquid delivery hose 58 is a factor in determining the rate of flow from the hose. This flow rate for a constant pressure head is then adjusted by adjusting the setting of the valve 60. When all factors influencing flow rate, including this hydrostatic pressure head, are maintained constant, a single setting of the valve 60 will be all that is needed to achieve a uniform flow of liquid 26 from the hose 58 regardless of the height of liquid in the supply chamber 10.

In the particular form of the invention shown in FIGS. 1 and 2, the vertical base plate 32 includes an integrally bonded layer of plastic magnetic material 62. This magnetic material 62 makes it possible to immediately install the apparatus of the invention at any convenient location such as a metallic animal watering trough wall 63. Such an installation is seen in FIGS. 1 and 2.

Also mounted with respect to the vertical base plate 32 is an L-shape float controlled arm 64. This arm 64 is physically mounted in a float controlled arm disc 66 which is itself pivotably mounted on a float control pivot pin 68. Pin 68 is fixedly mounted to extend outwardly from base plate 32, and has a sleeve 70 on it to limit the movement of a cover disc 72 and a nut 74 to insure that the float control arm disc 66 can pivot freely at all times.

As seen in FIG. 1, a rigid hollow extension elbow 78 is integral with flexible deformable liquid delivery hose 58 at the outer end of the hose, and this elbow is fixedly attached as at 80 to float controlled arm 64. The bottom end of the L-shape float controlled arm 64 fixedly supports a float 82.

In this first form of the invention, assuming that the animal water trough wall 63 forms a part of a watering trough 84 containing drinking water 86 therein, and assuming that when the drinking water is at the level indicated in full lines as at 88, the float 82 will be positioned as seen in full lines in FIG. 1. In this condition, the outer end of the hose extension elbow 78 will be open above the drinking water 86, and the liquid to be dispensed 26 can fall freely from the elbow 78 into the water 86.

A stopper block support arm 92 is fixedly mounted to the base plate 32, and a stopper block 94 extends outwardly from the lower end of its support arm 92 to be in alignment with the outer end of the elbow 78 as that elbow moves with the float controlled arm 64.

In a normal sequence of operations, it is desired to have liquid 26 added to the drinking water 86 by flowing at a fixed rate while the watering trough is in actual use, but to have the flow cut off during periods of no use as when the animals have substantially drained the water from the trough. This will be automatically accomplished using the stopper block 94. When the water in the trough is consumed to the point where the level of water in the trough as indicated by dotted line 96, the float 82 will take position as seen in dotted lines, and the lower end of the extension elbow 78 will be forced against the stopper block 94 to terminate further flow of liquid 26 from the hose 58.

For a particular liquid 26 to be dispensed, and utilizing a capillary liquid feed and drip tube 52, the size of the drops that drip from the tube are substantially exactly identical. Therefore, the device can be very easily calibrated by maintaining the hose 58 and elbow 78 in the position as seen in full lines in FIG. 1, positioning the liquid supply chamber filled with liquid 26 in its inverted position, and then adjusting the hose clamp vavle 60 to deliver the proper number of drops per minute from the capillary tube 52 as viewed through the sight glass 56 to achieve the rate of feed desired. Once this has been achieved, the delivery rate will not be changed by lowering of the level of the liquid 26 in the supply chamber 10. Rather, the rate of feed of liquid will remain constant because the hydrostatic head of pressure determining that feed rate is determined by the distance from the top of the liquid in the liquid pool 44 in basin 42 to the outer end of the hollow extension elbow 78.

There are many situations in which it is necessary or desirable to meter liquid flow from a liquid supply chamber at a constant rate and without the necessity of cutting off the flow through the use of a stopper block or something similar. Examples of this kind of use include feeding fertilizer and/or weed killer at a constant rate to an agricultural sprayer, or feeding liquid nutrients to a human patient intraveneously. In each case, the delivery hose such as the hose 58 will lead directly to the location for use of the liquid from the apparatus. Until the present invention, use of a capillary tube dripping inside of a sight glass to monitor the rate of delivery of the liquid and constant adjustment of a hose clamp valve such as valve 60 to compensate for the change in rate of flow due to the change of the height of the liquid inside of the liquid supply chamber has been necessary in many situations.

In accordance with the present invention, use of the capillary tube dripping into the sight glass is still an effective way to monitor the rate of delivery of the liquid; but once this rate is set by that means, or by any other means, the rate will remain substantially constant, and constant monitoring of the capillary tube through a sight glass is no longer necessary.

This invention will be particularly important where the desired rate of flow is substantially greater than that which can be accommodated by flow through a capillary tube. In such situations, the capillary tube and sight glass can be dispensed with, and some other means of controlling the rate of flow and monitoring it can be used.

Figure 3:
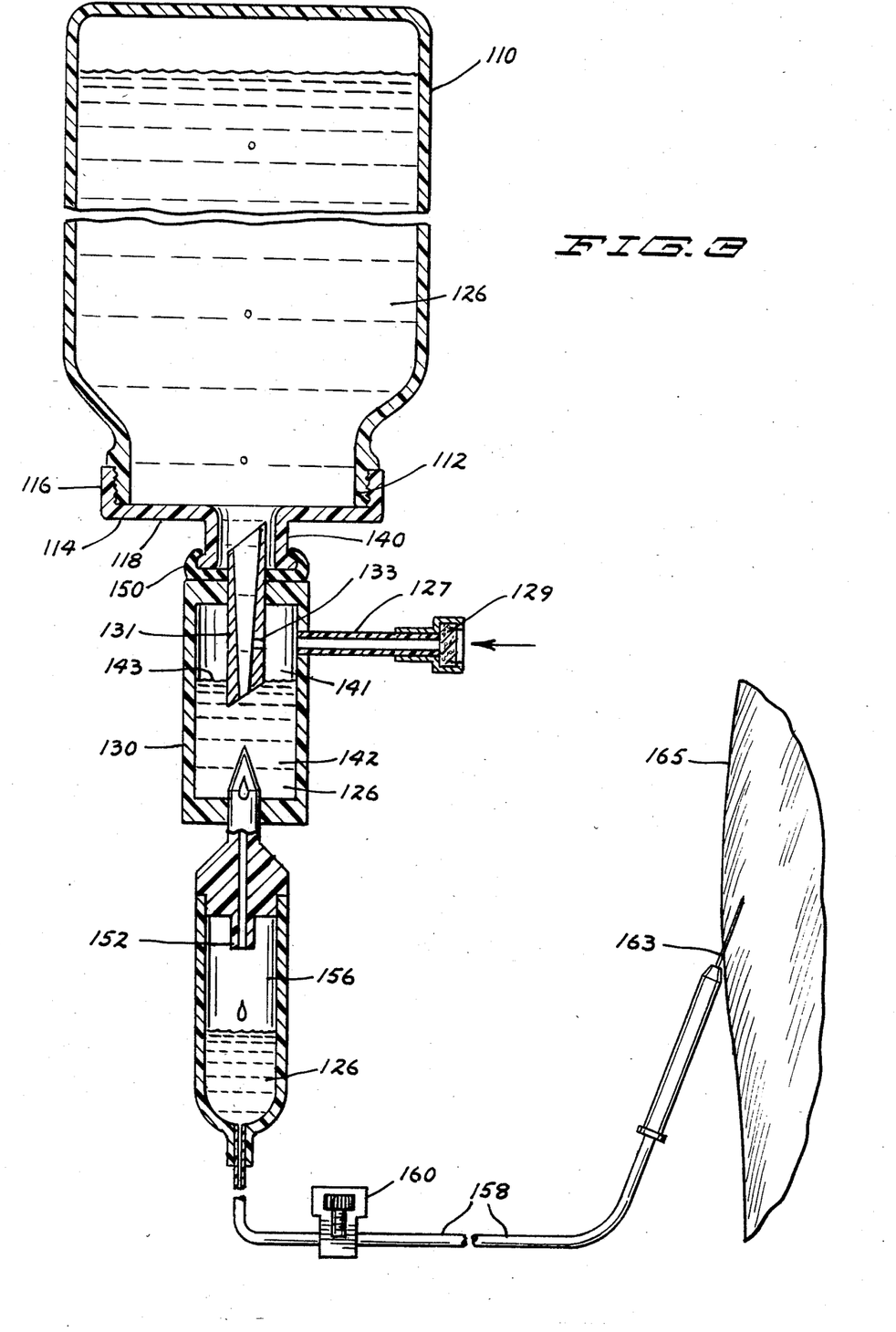
FIG. 3 is a transverse vertical sectional view similar to that seen in FIG. 2, but of an apparatus of a second form of the invention useful to supply blood plasma or liquid nutrients intraveneously into a human.
Figures 4, 5:
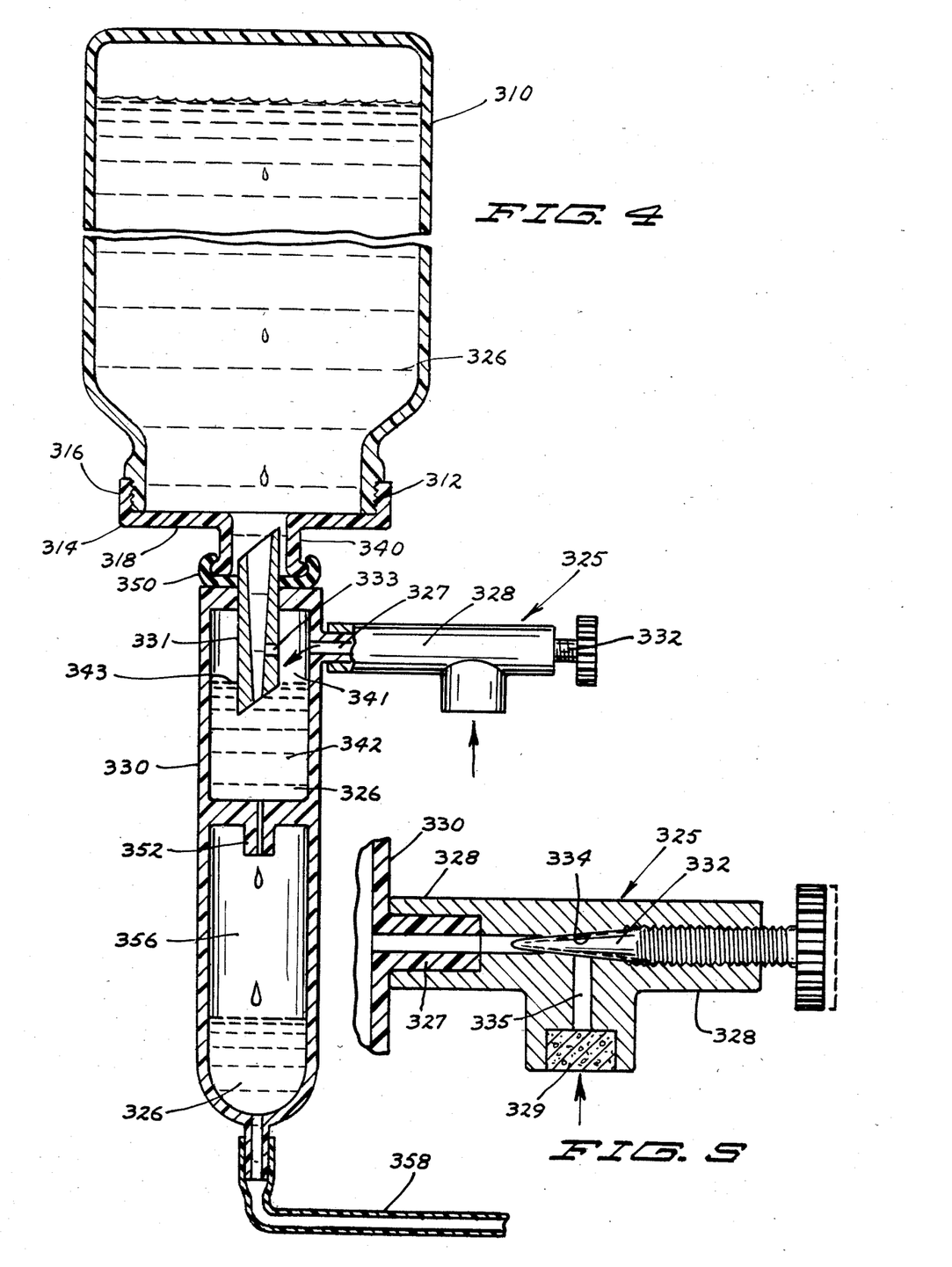
FIG. 4 is a transverse vertical sectional view similar to that seen in FIG. 3, but of an apparatus of a third form of the invention.
FIG. 5 is enlarged tranverse vertical sectional view of an atmospheric air or gas flow control valve with air filter of the apparatus of FIG. 4.
Figure 6:
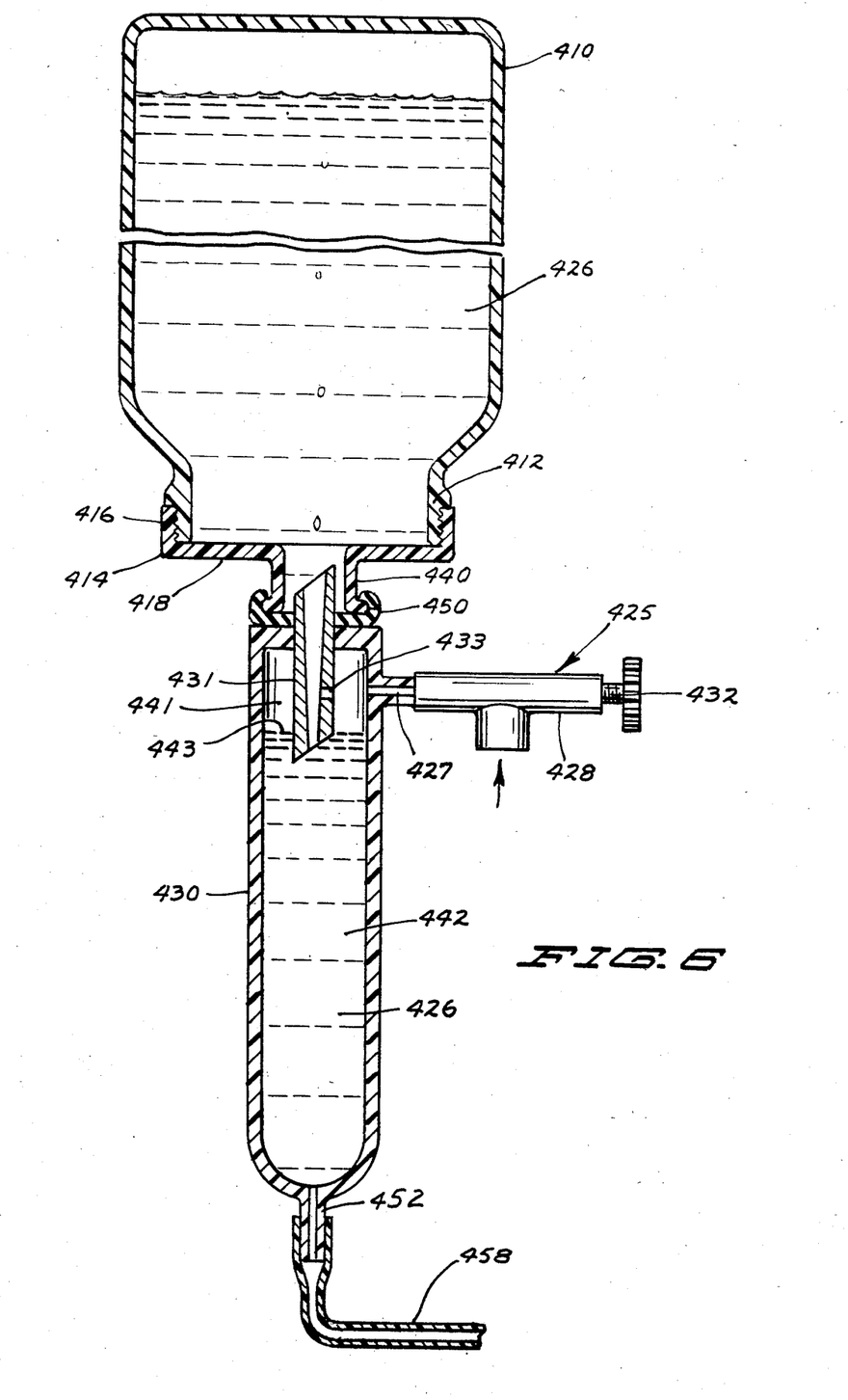
FIG. 6 is a transverse vertical sectional view similar to that seen in FIGS. 2, 3 and 4, but of an apparatus of a fourth form of the invention.

As particularly illustrated in FIGS. 3, 4 and 6, all being forms of the common invention, the supply tube is provided with an axial extending, tapered passage estending entirely therethrough with the decreased or smaller end of the passage being directed and opended to the atmospheric chamber or basin 141 and the increased or larger end of the passage being position within the neck portion 140 of the supply 110. As also illustrated in these various views, the bleed hole or aperture 133 enters through the side wall of supply tube 131 and passes therethrough to allow communication with the atmospheric chamber or basin 141 when the fluid level upper surface 143 closes the lower end of the supply 131 passage. It should be noted that this bleed hole 133 is spaced a determined distance from the lower end of supply tube 131 and this distance is determined in accordance with the size of bleed hole 133 and tapered aperture. Applicants have found that the diameter of the bleed hole 133 must be smaller than the diameter of the tapered passage of supply tube 131 for the admittance and non-air lock admittance of atmospheric air into the tube 131 for its ultimate release into the supply container 110. If the bleed hole is positioned to near the discharge or lower end of supply tube 131 such that it presents an air flow passage greater in diameter than the diameter of the tapered passage, an air lock will occur and the air from bleed passage 133 will not pass upwardly into the supply container 110. This combination therefore is necessary for continuous supply of fluid from container 110 to the basic chamber 142. Simply stated, the bleed hole must be positioned along the tapered passage of the supply tube 131 at a point where its diameter is less than the diameter of the tapered passage at point of entry. In certain instances, the applicants have found that a tapered passage with a bleed hole will allow continuous flow but applicants have found that the best results are obtained when the bleed hole spacing is correlated to tapering diameter as stated above.

Second Form of the Invention:

In a second form of the invention as seen in FIG. 3, a liquid supply chamber or bottle 110 includes an externally threaded neck portion 112 and a chamber cap or bottle cap 114 having an internally threaded skirt portion 116 threaded onto the neck portion 112 of the bottle 110 to bring a flat closure ortion 118 of the cap 114 into sealing relationship with the bottle neck portion 112.

The bottle cap 114 includes a neck portion 140 extending integrally downwardly from the closure portion 118. A rubber stopper 150 is designed to be removably mounted over the neck portion 140.

A reservoir 130 is constituted as a hollow cylindrical block with closed ends. A liquid supply tube 131 is permanently mounted in a top wall of the cylindrical reservoir block 130, and is open to a central portion of an atmospheric pressure basin 141 which is defined by the reservoir 130. An upper end of the liquid supply feed tube 131 is of shape and dimension to easily pierce the rubber stopper 150 and to thereafter be in sealing relation thereto. Liquid supply tube 131 at that point provides a liquid supply passage open from the interior of liquid supply chamber 110 to a central point in the atmospheric pressure basin 141. An air filter tube 127 is open through a side wall of the reservoir 130 at a position substantially above a horizontal plane passing through the bottom opening of the liquid supply tube 131. An air filter 129 is situated in an outermost end portion of the air filter tube. An air bleed hole 133 is open through the side wall of the liquid supply tube 131 at position substantially above the lower end of this supply tube.

A capillary liquid feed and drip tube 152 can be permanently or otherwise sealingly mounted in a bottom wall of the reservoir 130. A transparent cylindrical sight glass 156 is integrally connected to the feed tube 152 and extends downwaredly therefrom. A flexible deformable liquid delivery hose 158 is open to and extends downwardly from the bottom end of the sight glass 156, and an adjustable hose clamp valve 160 is manually adjustable to control the size of the minimum opening through the delivery hose.

In the form of the invention as shown, a hypodermic needle 163 is attached to the outer end of the delivery hose 158 to deliver a liquid to be dispensed 126 from the supply bottle 110 to the hose 158 and then subcutaneously into a living person or patient 165.

OPERATION OF SECOND FORM OF INVENTION

The liquid supply bottle or chamber 110 will be positioned with its neck portion 112 uppermost, and a supply of liquid to be dispensed 126 will be poured in. The rubber stopper 150 will then be sealingly fitted over an outer protrusion on the neck portion 140 of the chamber cap or bottle cap 114, and the liquid supply tube 131 will be forced through the stopper to lie in sealing relation to it and with the adjacent end wall of the reservoir tight against the stopper.

The entire assembly will then be inverted to position as seen in FIG. 3, and the liquid supply chamber will be supported by any usual or preferred means at position above that portion of the person 165 that is to be treated with fluid 126 from the hypodermic needle 163.

As soon as the bottle 110 is inverted, liquid 126 will flow out through the liquid supply tube 131 building up a liquid pool 142 in the atmospheric pressure basin 141. The pool will continue to form until its upper surface 143 closes off the lower end of the supply passage provided by the liquid supply tube 131. At that point, the atmospheric pressure in the upper portion of the basin 141 is sufficient to restrain further flow of liquid 126 from inside of the supply bottle 110 inasmuch as the contents of the supply bottle are, at that point, under a pressure less than atmospheric.

Atmospheric pressure acting through the small diameter bleed hole 133 on the liquid 126 in the liquid supply tube 130 is sufficient to prevent any flow of liquid 126 through the bleed hole 133.

With the adjustable hose clamp valve 160 entirely open to allow unrestricted passage through the flexible delivery hose 158, and with that delivery hose hanging straight down, the liquid 126 to be dispensed will flow through the capillary liquid feed and drip tube 152 into the sight glass 156 and from there out through the delivery hose 158. Once this flow is established, the outer end of the flexible hose 158 or the hypodermic needle 163 if it is at that time installed, can be raised above the upper surface 143 of the liquid 126 in the liquid pond 142, thus temporarily interrupting the flow. The hose clamp valve 160 can then be adjusted to begin to reduce the effective diameter of the delivery tube 158, and the outer end of the tube and hypodermic needle 163 can be lowered below the level of the surface 143 of the liquid pond 142. With the delivery hose 158 and the hypodermic needle 163 completely free of air bubbles, the hypodermic needle can be inserted at the prescribed place on person 165, and then the adjustable hose clamp valve 160 will be adjusted to permit the proper number of drops per minute to flow from the bottom of the capillary feed tube 152 into the sight glass 156.

As the level 143 of the liquid pool 142 drops in the basin 141, a point will be reached where part of the bottom of the liquid passage through liquid supply tube 131 will be uncovered, forming an imbalance between the pressure inside of the bottle 110 and atmospheric pressure such that air will be drawn into the supply tube 131 through the bleed hole 133, this air traveling to the uppermost portion of the liquid 126, will relieve the pressure inside of the bottle 110 so that more fluid 126 will flow into the basin 141 reestablishing the equilibrium. This action will continue until the supply bottle 110 has been emptied.

Because the upper surface 143 of the liquid pool 142 in the basin 141 of the hollow reservoir 130 is maintained constantly at atmospheric pressure, the effective hydrostatic pressure head forcing the liquid 126 out of basin 141, through liquid feed and drip tube 152, delivery hose 158 and the hypodermic needle 163 is always determined by the vertical distance between that upper surface 143 and the discharge point of the hypodermic needle. Thus where the patient receiving the liquid 126 remains stationary or at least on the same horizontal level, and the reservoir 130 is maintained in a single horizontal plane, the hydrostatic pressure at the delivery point of the needle will never change regardless of the level of the liquid in the bottle 110. Therefore, once the adjustable clamp valve 160 is properly adjusted to give the right number of drops per unit of time as prescribed by the doctor, for example, there is no need to readjust this clamp and the attendant need check the apparatus only to insure that there is still liquid in the bottle 110. There is no need to continually change the setting of the hose clamp valve 160 in an attempt to maintain the flow rate from the needle 163 somewhere near constant.

The second form of the invention is independent of the use of a capillary feed and drip tube discharging into a transparent sight glass. This structure can be replaced with some other means of monitoring and/or controlling the rate of flow from the bottom of the atmospheric pressure basin 141 in the reservoir 130 to its location for use, whether that use was as shown in FIG. 3 or was for adding chlorine to drinking water, chemicals to a swimming pool, or liquid chemicals to any kind of a liquid flow stream in an industrial process, for example.

Third Form of the Invention:

In a third form of the invention as seen in FIGS. 4 and 5, a liquid supply chamber or bottle 310 includes an externally threaded neck portion 312 and a chamber cap or bottle cap 314 having an internally threaded skirt portion 316 threaded onto the neck portion 312 of the bottle 310 to bring a flat closure portion 318 of the cap 314 into sealing relationship with the bottle neck portion 312.

The bottle cap 314 includes a neck portion 340 extending inwardly downwardly from the closure portion 318. A rubber stopper 350 is designed to be removably mounted over the neck portion 340.

A reservoir 330 is constituted as a hollow cylindrical block with closed ends. A liquid supply tube 331 is permanently mounted in a top wall of the cylindrical reservoir block 330, and is open to a central portion of an atmospheric pressure basin 341 which is defined by the reservoir 330. An upper end of the liquid supply tube 331 is of shape and dimension to easily pierce the rubber stopper 350 and to thereafter be in sealing relationship thereto. Liquid supply tube 331 at that point provides a liquid supply passage open from the interior of the liquid supply chamber 310 to a central point in the atmospheric pressure basin 341. An air access tube 327 is open through a side wall of the reservoir 330 at position substantially above a horizontal plane passing through the bottom opening of the liquid supply tube 331. An atmospheric air or gas flow control valve 325 includes a hollow barrel 328 in sealing relation to the air access tube 327, a needle valve stem 332 threadably mounted in the barrel 328 to be in operative relationship to a valve seat 334 which is provided in the barrel 328. A filtered air inlet passage 335 in barrel 328 opens to the central air passageway through the valve seat, and opens through an air filter 329 to position outside of barrel 328.

An air bleed hole 333 is open through the side wall of the liquid supply tube 331 at position substantially above the lower end of this supply tube.

As in the description of the Second Form of the Invention of FIG. 3, the passage through the supply tube 331 is tapered to have its lower, decreased diameter end within the atmospheric basin 342 and the bleed hole 333 communicates through the body of the tube 331 with such passage for introduction of atmospheric air into such passage with it ultimately rising into the supply container 310 for adjustment of air pressure therein and release of fluid therefrom. The tapered position is identical to that illustrated in FIG. 3 and the reasoning for such combination is the same.

A capillary liquid feed and drip tube 352 will be permanently or otherwise sealingly mounted in a bottom wall of the reservoir 330. A transparent cylindrical sight glass 356 is made integral with the reservoir 330 and extends downwardly therefrom. A flexible deformable liquid delivery hose 358 is open to and extends downwardly from the bottom end of the sight glass 356. This delivery hose can go to any usual or preferred location for use (not shown) as discussed in connection with the first two forms of the invention.

OPERATION OF THIRD FORM OF INVENTION

A liquid supply bottle or chamber 310 will be filled with a supply of liquid to be dispensed 326 while its neck portion 312 is uppermost, the rubber stopper 350 will be installed on the neck portion 340, and a liquid supply tube 331 will be forced through the stopper to lie in sealing relationship to it. This much of the entire assembly will then be inverted to the position as seen in FIG. 4, and the liquid supply chamber will be supported in any usual or preferred manner at position above the ultimate discharge point from the delivery hose 358.

As soon as bottle 310 is inverted, liquid 326 will flow out through the liquid supply tube 331 building up a liquid pool 342 in the atmospheric pressure basin 341. The pool will continue to form until its upper surface 343 closes off the lower end of the supply passage provided by the liquid supply tube 331. At that point, needle valve stem 332 will have been backed away from valve seat 334 to allow free access of filtered air through passageway 335, the central opening in the hollow barrel 328, the central opening in air access tube 327, and into an upper portion of the basin 341. With free access of atmospheric pressure thus being present in the upper portion of the basin 341, that pressure is sufficient to restrain further flow of liquid 326 from inside of the supply bottle 310 inasmuch as the contents of the supply bottle are, at that point, under a pressure less than atmospheric.

Atmospheric pressure acting through the small diameter bleed hole 333 on the liquid 326 in the liquid supply tube 331 is sufficient to prevent any flow of liquid 326 through the bleed hole 333.

With no restriction to flow of atmospheric air into the upper portion of the atmospheric pressure basin 341, liquid 326 will continue to flow through the capillary liquid feed and drip tube 352 into the sight glass 356 and from there, out through delivery hose 358.

Once this flow is established, the needle valve stem 332 can be rotated manually into sealing relationship with the needle valve seat 334, thus temporarily shutting off atmospheric pressure basin 341 from access to atmospheric pressure. At this point, the flow of liquid 326 may continue until the air bleed hole 333 is closed off by it. The flow through the apparatus can then be reinstated by slowly backing off the valve stem 332 to allow atmospheric pressure to again enter the reservoir basin 341. An action such as described in connection with the second form of the invention will again be set up, and the positioning of the valve stem 332 with respect to the valve seat 334 will be set such that atmospheric air will bleed into the atmospheric pressure basin 341 at a rate to cause the desired rate of flow of liquid 326 outwardly through delivery tube or hose 358. This rate of delivery can be determined, as pointed out in connection with the earlier forms of the invention, by counting the number of drops per unit of time that fall from the capillary tube 352. Other means of metering the flow can also be used. By calibrating the angular relationship of the valve stem 332 with respect to the barrel 328 of the air or gas flow control valve 325, exact predetermined flow rates can be instantaneously reestablished. Furthermore, other apparatus of any usual or preferred construction can be operably connected to the valve stem 332 to automatically increase and/or decrease the flow of liquid 326 from the delivery tube 358 pursuant to any desired parameters. For example, this flow rate can be controlled to vary directly with respect to the flow rate of a larger body of fluid into which the liquid 326 is being dispensed.

Fourth Form of the Invention:

In a fourth form of the invention as seen in FIG. 6, a liquid supply chamber or bottle 410 includes an externally threaded neck portion 412 having a chamber cap or bottle cap 414 having an internally threaded skirt portion 416 threaded onto the neck portion 412 of the bottle 410 to bring a flat closure portion 418 of the cap 414 into sealing relationship with the bottle neck portion 412.

The bottle cap 414 includes a neck portion 440 extending integrally downwardly from the closure portion 418. A rubber stopper 450 is designed to be removably mounted over the neck portion 440.

A reservoir 430 is constituted as a test tube-like hollow cylindrical block with closed ends. A liquid supply tube 431 is permanently mounted in a top wall of the reservoir block 430, and is open to an upper portion of an atmospheric pressure basin 441 which is defined by the reservoir 430. An upper end of the liquid supply tube 431 is of shape and dimension to easily pierce the rubber stopper 450 and to thereafter be in sealing relation to it. Liquid supply tube 431 at that point provides a liquid supply passage open from the interior of the liquid supply chamber 410 to a centrally positioned intermediate portion of the atmospheric pressure basin 441. An air access tube 427 is open through a side wall of the reservoir 430 at position substantially above a horizontal plane passing through the bottom opening of the liquid supply tube 431. An atmospheric air or gas flow control valve 425 has a hollow barrel 428 which is sealingly fastened to the air access tube 427. This flow control valve 425 includes a needle valve stem 432 rotatably mounted in the barrel 428 to mate with a needle valve seat (not shown). The structure of the flow control valve 425 can be exactly the same as construction of the air or gas flow control valve 325 as seen in FIGS. 4 and 5 including the filtered air inlet passage and the air filter.

An air bleed hole 433 is open through the side wall of the liquid supply tube 431 at position substantially above the lower end of this supply tube.

As in the Second and Third Forms of the Invention, the supply tube 431 is provided with a tapered passage and the air bleed hole 433 communicates through the body of tube 431 with such a tapered passage and may, at the user's option and in accordance with the type of material being delivered, be positioned to prevent air lock and therefore insure release of fluid from container 410.

A liquid feed tube 452 opens from the bottom of the reservoir 430 into a liquid delivery tube 458 which extends downwardly from the bottom of the reservoir 430 to carry a liquid 426 which is being dispensed to any desired location for use.

OPERATION OF FOURTH FORM OF INVENTION

The liquid supply bottle or chamber 410 will be positioned with its neck portion 412 uppermost, and a supply of liquid to be dispensed 426 will be poured in. The rubber stopper 450 will then be sealingly fitted over an outer protrusion on the neck portion 440 of the chamber cap or bottle cap 414 and the liquid supply tube 431 will be forced through the stopper to lie in sealing relation to it.

The entire assembly to that point will then be inverted as seen in FIG. 6, and the liquid supply chamber will be supported in any usual or preferred manner at position above the desired delivery point of the liquid 426 from the delivery tube 458. Assuming, at this point, that the needle valve stem 432 is backed off sufficiently to allow access of the atmosphere through the atmospheric air or gas flow control valve 425 to the atmospheric pressure basin 441, liquid 426 will flow out through the liquid supply tube 431 building up a liquid pool 442 in the atmospheric pressure basin 441. The pool will continue to form until its upper surface 443 closes off the lower end of the supply passage provided by the liquid supply tube 431. At that point, the atmospheric pressure in the upper portion of the basin 441 is sufficient to restrain further flow of liquid 426 from inside of the supply bottle 410 inasmuch as the contents of the supply bottle are, at that point, under a pressure less than atmospheric.

Atmospheric presure acting through the small diameter bleed hole 433 on the liquid 426 in the liquid supply tube 431 is sufficient to prevent any flow of liquid 426 through the bleed hole 433.

In order to control the rate of flow of liquid 426 out of the liquid delivery tube 458, either the needle valve stem 432 can be turned in clockwise direction to completely seal off the needle valve seat, as explained in connection with the third form of the invention, or the needle valve stem 432 can be turned slowly toward the valve seat to restrict the rate of access of atmospheric air to the atmospheric pressure basin 441 until the desired flow is achieved. Measurement of the rate of flow from the delivery tube 458 can be accomplished in any usual or preferred manner. For example, the outside of a transparent or translucent liquid supply bottle 410 can be marked with volumetric graduations, and the flow from the bottle over an extended period for a particular setting of the flow control valve 425 can be recorded. Otherwise, the flow from the liquid delivery tube 458 can be directed into a graduated beaker, and the flow per unit of time determined in that manner. Other means of measuring will readily suggest themselves to those skilled in the art. For example, where liquid 458 is being added to a flowing body of drinking water to chlorinate or otherwise treat a municipal water supply, a transducer downstream can be used to generate a signal representative of the ratio of the liquid 426 to the total volume of drinking water, and that signal can be used to control the positioning of the flow control valve 425 to keep the ratio within predetermined acceptable parameters.

As described for the Second, Third and Fourth Forms of the Invention, the fluid flow passage through the supply tubes 131, 331 & 431 are tapered in upwardly increasing manner and the respective air bleed holes 133, 333 and 433 enter through the bodies of such tubes to communicate atmospheric pressure into the tube above the normally arranged lower end thereof. It should be noted that the lowermost ends of the tubes is angled with respect to the axial dimension of the tubes 131, 331 & 431 and this angularity, along with the tapered passage and bleed hole positioning all serve to prevent air locks in the system and thereby provide for smooth and continuous delivery of fluid from the containers 110, 310 and 410. It is well known, that when utilizing passages of relatively small diameters, air locks can and will occur and the surface tensions of material must similarly be accounted for. The applicants' slanting and tapered areas in conjunction with the bleed hole all lend assistance to elimination of these problems and insure smooth and continuous, as desired, flow of material from the respective containers to the respective head maintaining areas or chambers.

Although the present invention has been described with reference to preferred embodiments, workers skilled in the art will recognize that changes may be made in form and detail without departing from the spirit and scope of the invention.

What is claimed is:

1. In combination with an invertable and inverted liquid tight liquid supply bottle having a penetrable cover, an apparatus for gravity feed of liquid under constant hydrostatic pressure, such apparatus including:
   a. a reservoir defining a basin at one end thereof and having a receiving end on the opposite end thereof;
   b. means for introducing atmospheric pressure into said reservoir above said basin end;
   c. a liquid supply conduit connected to said receiving end having a tapered supply passage therethrough having an end for penetrating said cover and a delivery end, said tapered passge having its larger diameter end adjacent said penetrating end and its smaller diameter end arranged in spaced relation above said basin end and below said pressure introduction means; and
   d. a fluid flow passge means arranged in said basin end for delivery of fluid therefrom.

2. The apparatus of claim 1 wherein:
   a. means is provided to control the rate of flow of liquid from said fluid flow passage means.

3. The apparatus of claim 2 wherein:
   a. said flow control means includes valve means in operable relation to said fluid flow passage means.

4. The apparatus of claim 1 and;
   a. said liquid supply conduit having an air passage therethrough generally normal to said liquid flow passage means for introduction of atmospheric air into said passage.

5. The apparatus of claim 4 and;
   a. said atmospheric air introduction passage being of a first diameter and communicating with said liquid passage means at a position longitudinally thereof at which the diameter of said tapered passage for liquid is greater than said first diameter of said communicating passage.

6. The apparatus of claim 1 and;
   a. said reservoir providing a substantially closed body; and,
   b. said means for introducing atmospheric pressure into said reservoir including a passage formed through said reservoir.

7. The apparatus of claim 5 and;
   a. valve means arranged and constructed to control the communication through said atmospheric pressure introduction means.

8. The apparatus of claim 1 and;
   a. the smaller end of said liquid supply conduit being angularly arranged with respect to the longitudinal axis of the same.

* * * * *